United States Patent
Graff

(10) Patent No.: US 11,236,231 B2
(45) Date of Patent: Feb. 1, 2022

(54) SILICONE GUM EMULSION

(71) Applicant: ICM Silicones Group, CHT USA, Cassopolis, MI (US)

(72) Inventor: Robert W. Graff, Cassopolis, MI (US)

(73) Assignee: CHT USA INC., Cassopolis, MI (US)

(*) Notice: Subject to any disclaimer, the term of this patent is extended or adjusted under 35 U.S.C. 154(b) by 190 days.

(21) Appl. No.: 16/655,347

(22) Filed: Oct. 17, 2019

(65) Prior Publication Data

US 2020/0123384 A1 Apr. 23, 2020

Related U.S. Application Data

(60) Provisional application No. 62/747,699, filed on Oct. 19, 2018.

(51) Int. Cl.
*C08L 83/04* (2006.01)

(52) U.S. Cl.
CPC ........... *C08L 83/04* (2013.01); *C08L 2201/52* (2013.01); *C08L 2201/54* (2013.01); *C08L 2205/025* (2013.01); *C08L 2205/03* (2013.01)

(58) Field of Classification Search
CPC .. C08L 83/04; C08L 2201/52; C08L 2201/54; C08L 2205/025
See application file for complete search history.

(56) References Cited

U.S. PATENT DOCUMENTS

| | | | |
|---|---|---|---|
| 4,125,470 A | 11/1978 | Fenton et al. | |
| 5,879,671 A * | 3/1999 | Halloran | A61K 8/898 424/70.122 |
| 8,877,293 B2 | 11/2014 | Evans et al. | |
| 2005/0176601 A1* | 8/2005 | Samain | A61Q 19/04 510/119 |
| 2014/0308229 A1* | 10/2014 | Bouzeloc | C08K 5/17 424/70.122 |
| 2017/0204266 A1 | 7/2017 | Kennedy et al. | |

* cited by examiner

*Primary Examiner* — Margaret G Moore
(74) *Attorney, Agent, or Firm* — Barnes & Thornburg LLP; Scott D. Rothenberger

(57) ABSTRACT

An essentially solvent free emulsion is described comprising about 10 parts to about 80 parts of a silicone gum; about 1 part to about 20 parts of an amino-functionalized organopolysiloxane; about 1 part to about 20 parts of a nonionic surfactant; about 0.01 to about 5 parts acid; optionally, a silicone polyether; and optionally, an aqueous solution to equal 100 parts.

19 Claims, No Drawings

SILICONE GUM EMULSION

CROSS REFERENCE TO RELATED APPLICATIONS

This application claims priority to U.S. Provisional Application Ser. No. 62/747,699, filed Oct. 19, 2018, the content of which is expressly incorporated herein by reference for all purposes.

FIELD OF THE INVENTION

The invention relates generally to silicone gum emulsions that are devoid of aromatic solvent(s) and include a silicone gum, an amino-functionalized organopolysiloxane, a nonionic surfactant, an acid, an optional silicone polyether and optionally, an aqueous solution.

BACKGROUND OF THE INVENTION

High molecular weight linear polysiloxane with viscosities that exceed 20 million centipoise (cP), also known as silicone gums, find use in several applications including, for example, additives for slip and anti-mar additives in coatings, such as leather finishes and coatings and band ply lubricants used in the manufacture of tires. Due to the ultra-high viscosity of these materials they are often delivered in the form of an emulsion, however preparation of such emulsions is challenging often requiring special emulsifiers and equipment.

Preparation of aqueous mechanical emulsions of high molecular weight silicones is difficult due to the high viscosity of the silicone material. The emulsions are typically prepared using specialized surfactants or with the need to dilute the high viscosity silicone in a solvent which may be undesirable, such as volatile organic compounds, aromatic solvent or other environmentally unfriendly substances. High molecular weight silicones can also be emulsified using specialized equipment such as twin screw extruders. However, the costs for such equipment are relatively high, both from a capital and an operational standpoint.

Therefore, a need exists that overcomes one or more of the current disadvantages noted above.

BRIEF SUMMARY OF THE INVENTION

The present embodiments surprisingly provide, silicone gum emulsions can be mechanically prepared using simple commercially available reagents including a nonionic surfactant, an amino-functionalized organopolysiloxane, an acid and optionally a silicone polyether. The silicone gum emulsions described herein are free of aromatic solvent and are equal in dilution stability to industry standard commercially available products in the market. By stable it is meant that no creaming (flocculation of particles resulting in solids variance from top to bottom, this is often visually seen by a phase line) or oiling (irreversible separation of water insoluble materials) from the emulsion). At high concentration ~80% the emulsion is stable long term (most likely 2 years to indefinite) due to high viscosity. A common test is to dilute the emulsion between, 10-50% solids. Emulsions become less stable upon dilution, at this point the emulsions can be evaluated by centrifugation or long-term ageing for separation.

In one aspect, a composition is provided that includes about 10 parts to about 80 parts of a silicone gum; about 1 part to about 20 parts of an amino-functionalized organopolysiloxane; about 1 part to about 20 parts of a nonionic surfactant; about 0.01 to about 5 parts acid; optionally, a silicone polyether; and optionally, an aqueous solution to equal 100 parts.

The emulsions are readily prepared without the need for specialized and expensive twin extruders or undesired solvents, such as aromatic solvents. Thus the emulsions are suitable for use in the personal care industry.

The emulsions described herein have the unexpected advantage of reduced particle size and better stability when using both acid(s) and amino-siloxane(s) in contrast to when an acid and/or amino-siloxane is/are not present.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

In one embodiment, a composition is provided that includes about 10 parts to about 80 parts of a silicone gum; about 1 part to about 20 parts of an amino-functionalized organopolysiloxane; about 1 part to about 20 parts of a nonionic surfactant; about 0.01 to about 5 parts acid; optionally, a silicone polyether; and optionally, an aqueous solution to equal 100 parts.

The embodiments described herein rely on the theory, but are not limited to, that the amino-functionalized organopolysiloxane is acting as a co-emulsifier. Treatment of the amino-functionalized organopolysiloxane with acid protonates the amines on the polymer backbone so that they become cationic. This, it is believed, allows the amino-functionalized organopolysiloxane to become amphiphilic and "self emulsifying".

The term "silicone gum" refers to predominately linear organopolysiloxanes having a sufficiently high molecular weight to provide kinematic viscosities greater than 500 thousand cSt at 25° C. For example, the formula molecular weight can be about 250,000. While any organopolysiloxane considered as a gum may be selected as a component, typically the silicone gum is a diorganopolysiloxane gum with a molecular weight sufficient to impart a William's plasticity number of at least about 30 as determined by the American Society for Testing and Materials (ASTM) test method 926. The silicon-bonded organic groups of the diorganopolysiloxane may be substituted. For example, the organic groups may be independently selected from alkyl or halogenated alkyl groups. In one embodiment, the organic groups may be exemplified by alkyl groups having 1 to 20 carbon atoms, such as methyl, ethyl, propyl, butyl, pentyl and hexyl; cycloalkyl groups, such as cyclohexyl and cycloheptyl; aryl groups having 6 to 12 carbon atoms, such as phenyl, tolyl and xylyl; aralkyl groups having 7 to 20 carbon atoms, such as benzyl and phenylethyl; and halogenated alkyl groups having 1 to 20 carbon atoms, such as 3,3,3-trifluoropropyl and chloromethyl.

In another embodiment, the diorganopolysiloxane can be a homopolymer, a copolymer or a terpolymer containing such organic groups. Examples include, but are not limited to, homopolymers comprising dimethylsiloxy units, homopolymers comprising 3,3,3-trifluoropropylmethylsiloxy units, copolymers comprising dimethylsiloxy units and phenylmethylsiloxy units, copolymers comprising dimethylsiloxy units and 3,3,3-trifluoropropylmethylsiloxy units, copolymers of dimethylsiloxy units and diphenylsiloxy units and terpolymers of dimethylsiloxy units, diphenylsiloxy units and phenylmethylsiloxy units.

The silicon-bonded organic groups of the diorganopolysiloxane can be selected from alkenyl groups having 1 to 20 carbon atoms, such as, but not limited to, vinyl, allyl, butenyl, pentenyl, hexenyl, or dodecenyl. Examples include dimethylvinylsiloxy-endblocked dimethylpolysiloxanes; dimethylvinylsiloxy-endblocked dimethylsiloxane-methylvinylsiloxane copolymers; dimethylvinylsiloxy-endblocked methylphenylpolysiloxanes; and dimethylvinylsiloxy-endblocked methylphenylsiloxane-dimethylsiloxane-methylvinylsiloxane copolymers.

The silicon-bonded organic groups of the diorganopolysiloxane may also be selected from various organofunctional groups such as amino, amido, mercapto, or epoxy functional groups.

The molecular structure of the diorganopolysiloxane may be exemplified by straight-chain (linear) unbranched structures and by partially branched straight-chain structures. In some embodiments, straight-chain (unbranched) structures are utilized.

In one embodiment, the silicone gum can be any one of the above-described silicone gum or any combination thereof. In another embodiment, the silicone gum is a hydroxy terminated polydimethylsiloxane gum having a viscosity of at least 10 million cP at 25° C. at 0.01 Hz.

The silicone gum may be used in combination with other organopolysiloxanes. Organopolysiloxanes are polymers containing siloxane units independently selected from $(R_3SiO_{1/2})$, $(R_2SiO_{2/2})$, $(RSiO_{3/2})$ or $(RSiO_{4/2})$ siloxy units, where R may be any monovalent organic group. When R is a methyl group in the $(R_3SiO_{1/2})$, $(R_2SiO_{2/2})$, $(RSiO_{3/2})$ or $(RSiO_{4/2})$ siloxy units of an organopolysiloxane, the siloxy units are commonly referred to as M. D. T. and Q units respectively. These siloxy units can be combined in various manners to form cyclic, linear, or branched structures. The chemical and physical properties of the resulting polymeric structures can vary. For example organopolysiloxanes can be volatile or low viscosity fluids, high viscosity fluids/gums, elastomers or rubbers, and resins depending on the number and type of siloxy units in the average polymeric formula. R may be any monovalent organic group, alternatively R is a hydrocarbon group containing 1 to 30 carbons, alternatively R is an alkyl group containing 1 to 30 carbon atoms, or alternatively R is methyl.

The silicone gum incorporated into the composition can be in the range of from about 5 parts to about 90 parts, in particular from about 15 parts to about 70 parts, from about 25 parts to about 65 parts, from about 30 parts to about 60 parts, from about 40 parts to about 50 parts and all ranges and individual values from about 5 parts to about 90 parts, e.g., 5, 6, 7, 8, 9, 10 parts, 11 parts, 12 parts, 13 parts through 78 parts, 79 parts 80 parts, 81 parts, through 90 parts.

The terms "amino-functional organopolysiloxane", "amino-functionalized organopolysiloxane", or "amino-functional(ized) polysiloxane" are characterized by having at least one of the R groups in the formula $R_nSiO_{(4-n)/2}$ be an amino functional group. The amino functional group may be present on any siloxy units having an R substituent. That is, they may be present on any $(R_3SiO_{1/2})$, $(R_2SiO_{2/2})$, or $(RSiO_{3/2})$ unit, and is designated in the formulas herein as $R^N$. The amino-functional organic group R is illustrated by groups having the formula; $-R^3NHR^4-$, $-R^3NR_2^4-$, or $-R^3NHR^3NHR^4-$, wherein each R is independently a divalent hydrocarbon group having at least 2 carbon atoms, and $R^4$ is hydrogen or an alkyl group. Each $R^3$ is typically an alkylene group having from 2 to 20 carbon atoms. $R^3$ is illustrated by groups such as: $-CH_2CH_2-$, $-CH_2CH_2CH_2$, $-CH_2CHCH_3-$, $-CH_2CH_2CH_2CH_2-$, $-CH_2CH(CH_3)CH_2-$, $-CH_2CH_2CH_2CH_2CH_2-$, $-CH_2CH_2CH_2CH_2CH_2CH_2-$, $-CH_2CH_2CH(CH_2CH_3)CH_2CH_2CH_2-$, $-CH_2CH_2CH_2CH_2CH_2CH_2CH_2CH_2$ and $-CH_2CH_2CH_2CH_2CH_2CH_2CH_2CH_2CH_2CH_2-$. The alkyl groups $R^4$ are as illustrated above for R. When R is an alkyl group, it is typically methyl.

Some examples of suitable amino-functional hydrocarbon groups are: $-CH_2CH_2NH_2$, $-CH_2CH_2CH_2NH_2$, $-CH_2CH(CH_3)NH_2$, $-CH_2CH_2CH_2CH_2NH_2$, $-CH_2CH_2CH_2CH_2CH_2NH_2$, $CH_2CH_2CH_2CH_2CH_2CH_2NH_2$, $-CH_2CH_2NHCH_3$, $-CH_2CH_2CH_2NHCH_3$, $-CH_2CH(CH_3)CH_2NHCH_3$, $-CH_2CH_2CH_2CH_2NHCH_3$, $CH_2CH_2NHCH_2CH_2NH_2$, $\geq CH_2CH_2CH_2NHCH_2CH_2NH_2$, $-CH_2CH_2CH_2NHCH_2CH_2CH_2NH_2$, $-CH_2CH_2CH_2CH_2NHCH_2CH_2CH_2NH_2$. $CH_2CH_2NHCH_2CH_2NHCH_3$, $CH_2CH_2CH_2NHCH_2CH_2CH_2-NHCH_3$, $CH_2CH_2CH_2CH_2NHCH_2CH_2CH_2NHCH_3$ $CH_2CH_2NHCH_2CH_2NHCH_2CH_2CH_3$. Alternatively, the amino functional group is $-CH_2CH(CH_3)CH_2NHCH_2CH_2NH_2$.

The amino-functional organopolysiloxane used may be selected from those having the average formula:

$$[R_3SiO_{1/2}][R_2SiO_{2/2}]_a[RR^NSiO_{2/2}]_b[R_3SiO_{1/2}]$$

and where; a is 1-1000, alternatively 1 to 500, alternatively 1 to 200, b is 1-100, alternatively 1 to 50, alternatively 1 to 10, R is independently a monovalent organic group, alternatively R is a hydrocarbon containing 1-30 carbon atoms, alternatively R is a monovalent alkyl group containing 1-12 carbons, or alternatively R is a methyl group; $R^N$ is as defined above. The amino-functional organopolysiloxane used in combination with the silicone gum may also be a combination of any of the aforementioned amino-functional organopolysiloxanes.

The amine structures can include aromatic amines, alkylene aryl amines and include quaternary ammonium (salts) functional siloxanes, generally the amine could be quantized by organic functionalization resulting in a permanent charge, such as $R_4N^+B^-$, where B is all common counter ions including halogens, sulfates, nitrates, etc. and each $R_4$ is an alkyl or aryl group.

In one embodiment, the amino-functionalized organopolysiloxane component comprises at least one side chain component A having the general formula:

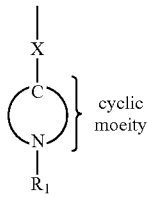

$R_1$ is an H or a $C_1$-$C_5$ hydrocarbon, and X is a $C_1$-$C_{10}$ hydrocarbon, a heteroatom or

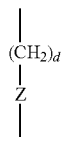

wherein Z is a heteroatom and d is 0 to about 6. Non-limiting examples of heteroatoms useful in this invention includes N. O, S and P. In one embodiment, Z is O (oxygen) and d is about 3. In another embodiment, the cyclic moiety of the side chain component is saturated. In another embodiment, the cyclic moiety is substituted. For example, the a side chain component A of the amino-functionalized organopolysiloxane component may include the general formula:

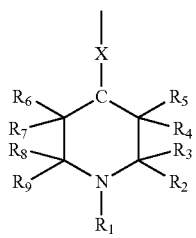

wherein $R_1$, $R_2$, $R_3$, $R_4$, $R_5$, $R_6$, $R_7$, $R_8$ and $R_9$ are independently a H, a $C_1$-$C_{10}$ hydrocarbon, an ester, carboxyl or a halogen, and X is a $C_1$-$C_{10}$ hydrocarbon, a heteroatom or

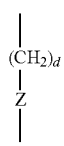

wherein Z is a heteroatom and d is 0 to about 6. X is a $C_1$-$C_5$ hydrocarbon or a heteroatom. In one embodiment, X is a heteroatom selected from the group consisting of N, O, Si, P. and S. In one embodiment, $R_1$, $R_4$, $R_5$ and $R_7$ are all hydrogen atoms and $R_2$, $R_3$, $R_8$ and $R_9$ are $C_1$ alkyls. Also, in an embodiment, the cyclic moiety is a 5 or 6 member ring.

For example, a side chain component A of an amino-functionalized organopolysiloxane has the general formula:

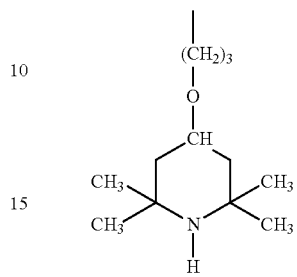

such as propoxytetramethyl piperidinyl dimethicone

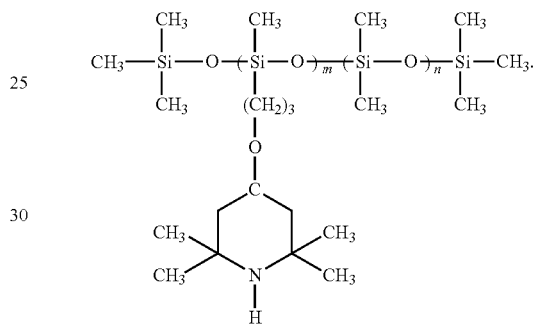

Another example of an amino-functionalized organopolysiloxane includes amodimethicone, with a molecular formula of $C_{15}H_{42}N_2O_3Si_4$ depicted as:

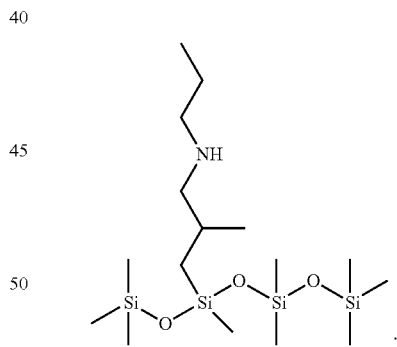

The amino-functionalized organopolysiloxane incorporated into the composition can be in the range of from about 0.1 part to about 50 parts, in particular from about 2 parts to about 15 parts, from about 5 parts to about 12 parts, from about 7 parts to about 10 parts, from about 8 parts to about 12 parts and all ranges and individual values from about 0.1 part to about 50 parts, e.g., 0.1 part, 0.2 parts, 0.3 parts, 0.4 parts, 2 parts, 3 parts, 4 parts through 18 parts, 19 parts 20 parts, 45 parts, 46 parts, 47 parts, 48 parts, 49 parts and 50 parts.

The term "non-ionic surfactant" or "nonionic surfactant" refers to a surfactant, in which the total number of electrons is equal to the total number of protons, giving it a net neutral or zero electrical charge. One suitable class of non-ionic surfactants includes the Pluronic® poloxamers.

Poloxamers are nonionic triblock copolymers composed of a central hydrophobic chain of polyoxypropylene (poly (propylene oxide)) flanked by two hydrophilic chains of polyoxyethylene (poly(ethylene oxide)). Poloxamers are also known by the trade name Pluronics®.

Because the lengths of the polymer blocks can be customized, many different poloxamers exist, that have slightly different properties. For the generic term "poloxamer," these copolymers are commonly named with the letter "P" (for poloxamer) followed by three digits, the first two digits "x" (times) 100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic® tradename, coding of these copolymers starts with a letter to define its physical form at room temperature (L=liquid, P=paste, F=flake (solid)) followed by two or three digits. The first digit (two digits in a three-digit number) in the numerical designation, multiplied by 300, indicates the approximate molecular weight of the hydrophobe; and the last digit×10 gives the percentage polyoxyethylene content (e.g., L61=Pluronic with a polyoxypropylene molecular mass of 1,800 g/mol and a 10% polyoxyethylene content). In the example given, poloxamer 181 (P181)=Pluronic L61.

The term "Pluronic® 10R5 surfactant block copolymer" refers to polyoxypropylene-polyoxyethylene block copolymer, having the CAS Reg. No. 9003-11-6.

Other nonionic surfactants include, but are not limited to, fatty alcohols, polyoxyethylene glycol alkyl ethers (BrIJ), polyoxypropylene glycol alkyl ethers, glucoside alkyl ethers, polyoxyethylene glycol octylphenol ethers, polyoxyethylene glycol alkylphenol ethers, glycerol alkyl esters, polyoxyethylene glycol sorbitan alkyl esters, sorbitan alkyl esters, cocamide MEAs, cocamide DEAs, dodecyl dimethylamine oxides, block copolymers of polyethylene glycol and polypropylene glycols.

Suitable fatty alcohols include, but are not limited to, cetyl alcohol, stearyl alcohol, cetostearyl alcohol (consisting predominantly of cetyl and stearyl alcohols) and oleyl alcohol.

Suitable polyoxyethylene glycol alkyl ethers, include but are not limited to (BRIJ), for example $CH_3-(CH_2)_{10-16}-(O-C_2H_4)_{1-25}-OH$, or octaethylene glycol monododecyl ether or pentaethylene glycol monododecyl ether.

Suitable polyoxypropylene glycol alkyl ethers include $CH_3-(CH_2)_{10-16}-(O-C_3H_6)_{1-25}-OH$.

Suitable glucoside alkyl ethers include $CH_3\geq(CH_2)_{10-16}-(O-Glucoside)_{1-3}-OH$, and, for example, include decyl glucoside, lauryl glucoside, and octyl glucoside.

Suitable polyoxyethylene glycol octylphenol ethers include $C_8H_{17}-(C_6H_4)-(O-C_2H_4)_{1-25}-OH$. One exemplary material is TRITON X-100.

Suitable polyoxyethylene glycol alkylphenol ethers include $C_9H_{19}-(C_6H_4)-(O-C_2H_4)_{1-25}-OH$. One example is Nonoxynol-9.

In one aspect, a suitable glycerol alkyl ester is glyceryl laurate.

In another aspect, a suitable polyoxyethylene glycol sorbitan alkyl ester is polysorbate.

In still another aspect, suitable sorbitan alkyl esters are referred to as SPAN, e.g., SPAN-20, sorbitan monolaurate.

Nonionic surfactants additionally include polymeric surfactants such as polyvinyl alcohol (PVA) and polyvinylmethylether.

Some additional non-ionic surfactants include ethoxylated alcohols sold under the trademark Novel TDA® (Sasol North America, Houston, Tex.) and TERGITOL® (The Dow Chemical Company, Midland, Mich.). Some examples are TERGITOL TMN-6, an ethoxylated alcohol known as ethoxylated trimethylnonanol; and various of the ethoxylated alcohols, i.e., the 12-14 carbon atoms secondary alcohol ethoxylates, sold under the trademarks TERGITOL® 15-S-5, TERGITOL® 15-S-12, TERGITOL® 15-S15, TERGITOL® 15-S-30, TERGITOL® 15-S-40, Novel TDA9®, Novel TDA40® and Novel TDA150®. Surfactants containing silicon atoms may also be used.

The nonionic surfactant incorporated into the composition can be in the range of from about 0.5 part to about 40 parts, in particular from about 2 parts to about 15 parts, from about 5 parts to about 12 parts, from about 7 parts to about 10 parts, from about 8 parts to about 12 parts and all ranges and individual values from about 0.5 part, 0.6 parts, 0.7 parts, 0.8 parts, 0.9 parts, 1 part to about 40 parts, e.g., 1 parts, 2 parts, 3 parts, 4 parts through 18 parts, 19 parts, 20 parts through 35 parts, 36 parts, 37 parts, 38 parts, 39 parts and 40 parts.

The term "acid" refers to a material used to protonate the amino-functional organopolysiloxanes, specifically the amine functionality resulting in a positive charge. Any substance that can protonate the amine is suitable as an acid. It can be selected from organic or inorganic acids. Suitable acids are exemplified by mineral acids such as sulfuric or hydrochloric acid or organic acids such as acetic acid, trifluoracetic acid or organo-sulfonic acids or other carboxylic acids or mixtures thereof.

The acid incorporated into the composition can be in the range of from about 0.01 part to about 10 parts, in particular from about 0.1 part to about 4.5 parts, from about 0.2 parts to about 4 parts, from about 0.5 parts to about 3.5 parts, from about 0.75 parts to about 3 parts and all ranges and individual values from about 0.01 part to about 10 parts, e.g., 0.01 parts, 0.02, 0.03, 0.04, 2.1 parts, 3.02 parts, 4.56 parts, 5 parts, 5.5 parts, 6 parts, 6.5 parts, 7 parts, 7.7 parts, 8 parts, 8.8 parts, 9 parts, 9.4 parts and 10 parts.

The term "silicone polyether" refers to a polydiorganosiloxane-polyoxyalkylene copolymer containing at least one polydiorganosiloxane segment and at least one polyoxyalkylene segment. The polyoxyalkylene segments may be bonded to the polydiorganosiloxane segments with silicon-oxygen-carbon bonds and/or with silicon-carbon bonds. The polydiorganosiloxane segments of the polydiorganosiloxane-polyoxyalkylene copolymer consist essentially of siloxane units which are interlinked by Si—O—Si linkages and which have the general formula:

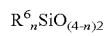

wherein n is 0, 1, 2 or 3, $R^6$ is independently a methyl, ethyl, vinyl, phenyl, or divalent group bonding a polyoxyalkylene segment to the polydiorganosiloxane segment. The siloxane units can be arranged in such a way as to produce linear or branched polydiorganosiloxane segments, and the linear or branched polydiorganosiloxane segments may be non-crosslinked or crosslinked.

The number average molecular weight of the polydiorganosiloxane having one or more polyoxyalkylene segments is about 1000 to about 2,000,000.

The silicone polyether component comprises a polyoxyalkylene group which can be polyoxyethylene (EO) designated by $(C_2H_4O)_r$ wherein r is from 1 to 500. The polyoxyalkylene group may also contain oxypropylene (PO) units designated by $(C_3H_6O)_s$ wherein s is from 0 to 100, oxybutylene units $(C_4H_8O)_t$ wherein t is from 0 to 50, or mixtures thereof. When the polyoxyalkylene group comprises a mixture of $(C_2H_4O)_r$, $(C_3H_6O)_s$ and/or $(C_4H_8O)_t$ units, the oxyalkylene groups are typically randomized but can exist as blocked structures. The content of the EO and/or PO in the silicone polyether is such that the silicone polyether is water soluble or water dispersible.

Representative examples of suitable commercially available non-ionic surfactants include but are not limited to ethylene oxide dimethylsiloxanes and propylene oxide/ethylene oxide block copolymer dimethylsiloxanes sold under the trade name Beausil Wax and Beausil PEG by the CHT Group, PEL-SIL by Ele Corporation, or DOWSIL™ and XIAMETER™ by the Dow Chemical Company.

The silicone polyether can be present from about 0.1 to about 40 parts, in particular from about parts to about 35 parts, from about 5 parts to about 30 parts, from about 7 parts to about 25 parts, from about 8 parts to about 20 parts and all ranges and individual values from about 0.1 part, 0.6 parts, 0.7 parts, 0.8 parts, 0.9 parts, 1 part to about 40 parts, e.g., 1 part, 2 parts, 3 parts, 4 parts through 18 parts, 19 parts, 20 parts through 35 parts, 36 parts, 37 parts, 38 parts, 39 parts and 40 parts.

The compositions described herein can include an aqueous solvent, such as water. In particular no solvent is present in the compositions described herein, e.g., emulsions, other than water. In some embodiments, a cosolvent, such as a monohydridic or polyhydridic alcohol can be included with the water to provide an aqueous solution. Suitable alcohols include, for example, methanol, ethanol, propanol, isopropanol, ethylene glycol, propylene glycol, low molecular weight polyethylene glycols, 2-methoxyethanol (methyl cellosolve), low molecular weight polypropylene glycols and glycol ethers, including Dowanol™ and generally $C_1$ through $C_{20}$ alkyl or alkylene compounds that are hydroxylated with one or more hydroxyl groups.

Generally, the range of an aqueous solution in the composition is from about 1 part to about 50 parts, from about 2 parts to about 45 parts, from about 5 parts to about 40 parts, from about 10 parts to about 30 parts, or from about 15 parts to about 25 parts and all ranges and individual values from about 1 part to about 50 parts, e.g., 1 part, 2 parts, 3 parts, 4 parts, 15 parts through 35 parts, 46 parts, 47 parts, 48 parts, 49 parts and 50 parts.

When a cosolvent is used in combination with water, the range is from about 0.1 part to about 2 parts, from about 0.5 parts to about 1.5 parts, from about 0.75 parts to about 1 part, from about 0.5 parts to about 1 part and all ranges and individual values from about 0.1 part to about 2 parts, e.g., 0.1 parts, 0.2, 0.3, 0.4, 0.8 parts, 1.2 parts, 1.4 parts and 2 parts.

The combination of the amino-functionalized organopolysiloxane and an acid, provides unexpected and surprising advantages that the resultant emulsions described herein have unique Mv, $D_{90}$ and $D_{99}$ particle size(s). Additionally, the resultant emlusions described herein are stable.

Typical Mv ranges of the emulsion particle size are from about 1 μm to about 5.5 μm, more particularly, from about 1.1 μm to about 5.2 μm and even more particularly from about 2 μm to about 3.5 μm.

Typical $D_{90}$ ranges of the emulsion particle size are from about 1.3 μm to about 8.5 μm, more particularly from about 2 μm to about 5 μm and even more particularly from about 3 μm to about 4 μm.

Exemplary $D_{99}$ ranges of the particle size are from about 1.5 μm to about 12 μm, more particularly from about 2 μm to about 10 μm and even more particularly from about 3 μm to about 6.5 μm.

The process of combining and mixing components silicone gum A), amino-functionalized organopolysiloxane B), nonionic surfactant C), acid D), optional silicone polyether E) and optional aqueous solution F) can occur in a single step or multiple step process. Thus, components A), B), C), D), E) and F) may be combined in total, and subsequently mixed via any of the techniques described below. Alternatively, a portion(s) of components A), B), C), D), E) and F) may first be combined, mixed, and followed by combining additional quantities of either or both components and further mixing. One skilled in the art would be able to select optimal portions of components A), B), C), D), E) and F) for combing and mixing, depending on the selection of the quantity used and the specific mixing techniques utilized.

Mixing can be accomplished by any method known in the art to effect mixing of high viscosity materials. The mixing may occur either as a batch, semi-continuous, or continuous process. Mixing may occur, for example using, batch mixing equipment with medium/low shear include change-can mixers, double-planetary mixers, conical-screw mixers, ribbon blenders, double-arm or sigma-blade mixers; batch equipment with high-shear and high-speed dispersers include those made by Charles Ross & Sons (NY), Hockmeyer Equipment Corp. (NJ); batch mixing equipment such as those sold under the tradename Speedmixer(R); batch equipment with high shear actions include Banbury-type (CW Bra bender Instruments Inc., NJ) and Henschel type (Henschel mixers America, TX). Illustrative examples of continuous mixers/compounders include extruders single-screw, twin screw, and multi-screw extruders, co-rotating extruders. Such as those manufactured by Krupp Werner & Pfleiderer Corp (Ramsey, N.J.), and Leistritz (NJ); twin-screw counter-rotating extruders, two-stage extruders, twin-rotor continuous mixers, dynamic or static mixers or combinations of these equipment.

Furthermore, no solvents are added for the purpose of enhancing formation of an emulsion. As used herein, the phrase "essentially free of "solvents" means that solvents are not added to the components described herein in order to create a mixture of suitable viscosity that can be processed on typical emulsification devices. More specifically, "solvents" as used herein is meant to include any water immiscible low molecular weight organic or silicone material added to the non-aqueous phase of an emulsion for the purpose of enhancing the formation of the emulsion, and is subsequently removed after the formation of the emulsion, such as evaporation during a drying or film formation step. Thus, the phrase "essentially free of solvent" is not meant to exclude the presence of solvent in minor quantities in process or emulsions of the present invention. For example, there may be instances where certain components may contain minor amounts of solvent as supplied commercially. Small amounts of solvent may also be present from residual cleaning operations in an industrial process. In particular, the amount of solvent present should be less than 2% by parts of the mixture, and more particularly the amount of solvent should be less than 1% by parts of the mixture. Most particularly, aromatic solvent(s) is/are not present in the compositions/emulsions described herein.

The following paragraphs enumerated consecutively from 1 through 34 provide for various aspects of the present invention. In one embodiment, in a first paragraph (1), the present invention provides a composition comprising:

about 10 parts to about 80 parts of a silicone gum;

about 1 part to about 20 parts of an amino-functionalized organopolysiloxane;

about 1 part to about 20 parts of a nonionic surfactant;

about 0.01 to about 5 parts acid;
optionally, a silicone polyether; and
optionally, an aqueous solution to equal 100 parts of total composition.

2. The composition of paragraph 1, wherein the silicone gum comprises about 50 to about 70 parts.

3. The composition of paragraph 3, wherein the silicone comprises about 65 parts.

4. The composition of any of paragraphs 1 through 3, wherein the silicone gum comprises a homopolymer of dimethylsiloxane or is a hydroxyl terminated dimethylsiloxane.

5. The composition of any of paragraphs 1 through 4, wherein the silicone gum is a polydimethylsiloxane gum having a viscosity of at least 10 million cP at 25° C. at 0.01 Hz.

6. The composition of any of paragraphs 1 through 4, wherein the silicone gum is a hydroxy terminated polydimethylsiloxane gum having a viscosity of at least 10 million cP at 25° C. at 0.01 Hz.

7. The composition of any of paragraphs 1 through 6, wherein the amino-functionalized organopolysiloxane comprises about 5 parts to about 15 parts.

8. The composition of paragraph 7, wherein the amino-functionalized organopolysiloxane comprises about 10 parts.

9. The composition of any of paragraphs 1 through 8, wherein the amino-functionalized organopolysiloxane comprises the formula:

$$[R_3SiO_{1/2}][R_2SiO_{2/2}]_a[RR^NSiO_{2/2}]_b[R_3SiO_{1/2}]$$

wherein; a is 1-1000;
b is 1-100;
each R is independently a monovalent organic group;
$R^N$ is $-R^3NHR^4$, $-R^3NR_2^4$, or $-R^3NHR^3NHR^4$;
each $R^3$ is a $C_2$-$C_{20}$ alkyl group; and
each $R^4$ is a hydrogen or a $C_1$-$C_{20}$ alkyl group.

10. The composition of any of paragraphs 1 through 8, wherein the amino-functionalized organopolysiloxane comprises a $R^4N^+X^-$ quaternary ammonium siloxane.

11. The composition of any of paragraphs 1 through 10, wherein the nonionic surfactant comprises a secondary alcohol ethoxylate.

12. The composition of any of paragraphs 1 through 11, wherein the optional silicone polyether is present from about 2 parts to about 15 parts.

13. The composition of any of paragraphs 1 through 12, wherein the optional silicone polyether is an ethylene oxide/propylene oxide block copolymer silicone glycol.

14. The composition of any of paragraphs 1 through 13, wherein the acid is a carboxyl acid, organic acid or an inorganic mineral acid.

15. The composition of paragraph 14, wherein the acid is acetic acid.

16. The composition of any of paragraphs 1 through 15, wherein the composition is an emulsion.

17. The composition of any of paragraphs 1 through 16, wherein the emulsion does not include an aromatic solvent.

18. The composition of paragraph 17, wherein the aromatic solvent is xylene.

19. The composition of any of paragraphs 1 through 18, further comprising a non-aromatic solvent.

20. The composition of paragraph 19, wherein the non-aromatic solvent is a $C_1$-$C_{20}$ alkyl or alkylene monohydridic or polyhydridic alcohol.

21. The composition of any of paragraphs 1 through 17, wherein the composition does not include a solvent.

22. The composition of any of paragraphs 1 through 21, wherein the composition is suitable for personal care applications.

23. The composition of any of paragraphs 1 through 21, wherein the composition is suitable for coatings applications.

24. The composition of any of paragraphs 1 through 21, wherein the composition is suitable for leather finishing and leather coating applications.

25. The composition of any of paragraphs 1 through 21, wherein the composition is suitable for release coatings and release applications.

26. The composition of any of paragraphs 1 through 21, wherein Mv is from about 1 µm to about 5.5 µm.

27. The composition of any of paragraphs 1 through 21, wherein Mv is from about 1.1 µm to about 5.2 µm.

28. The composition of any of paragraphs 1 through 21, wherein Mv is from about 2 µm to about 3.5 µm.

29. The composition of any of paragraphs 26 through 28, wherein $D_{90}$ is from about 1.3 µm to about 8.5 µm.

30. The composition of any of paragraphs 26 through 28, wherein $D_{90}$ is from about 2 µm to about 5 µm.

31. The composition of any of paragraphs 26 through 28, wherein $D_{90}$ is from about 3 µm to about 4 µm.

32. The composition of any of paragraphs 26 through 31, wherein $D_{99}$ is from about 1.5 µm to about 12 µm.

33. The composition of any of paragraphs 26 through 31, wherein $D_{99}$ is from about 2 µm to about 10 µm.

34. The composition of any of paragraphs 26 through 31, wherein $D_{99}$ is from about 3 µm to about 6.5 µm.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

Example 1

Silicone Gum Emulsion Using a Silicone Polyether (SPE), Amine-Functionalized Organopolysiloxane co-emulsifier and Non-Ionic Surfactant.

In a 150 mL polypropylene cup were added 65 grams of a silicone gum of a viscosity of 20 million cP (Xiameter™ RBG-0910 Gum) (DOW Silicones Corporation), 5 grams of a EO/PO block co-polymer silicone glycol (cloud point 98 C) (Ele Pel-Sil™ 9690)(Siloxanes and Silicones, di-Me, 3-hydroxypropyl Me, ethoxylated propoxylated, Cloud Point, 1% Aq., ° C. 38-41, Viscosity at 25° C., cps 5000 Maximum) and 5 grams of amino-functionalized polyorganosiloxane with amine number >50 and viscosity <1000 cps (I-SF-736p) (ICM Products Inc., I-SF-736p). The contents were mixed in a Speed Mixer™ DAC 150FV for 60 seconds at 3400 rpm. The process was repeated until homogenous. To the contents was added 0.25 grams glacial acetic acid and a total of 5 grams of water over several additions assuring the mixture remained homogenous. The cup and its contents were spun in the Speed Mixer for 30 second after each addition. To the mixture, 2 grams of Tergitol 15-S-7 and a total of 5 grams water was added over several additions assuring the mixture remained homogenous. To the mixture, 3 grams of Tergitol 15-S-7 (a polyglycol ether; CAS Number: 68131-40-8) and a total of 10 grams water was added over several additions assuring the mixture remained homogenous. The resulting mixture was a thick white to slightly yellow emulsion with particle size Mv=3.4 µm, $D_{90}$=5.1 µm, $D_{99}$=6.9 µm.

Mv=mean volume (mean particle size by volume), D90=90% of particles by volume are less that this value, D99=99% of particles are less than this value. To compare long term stability of the products which is critical for their application, the sample prepared above and a commercially available competitive sample containing aromatic solvents were diluted to 15% solids. The samples were then monitored at 25° C. for five days by a Formulaction, Turbisan Lab Expert. Example 1=3.44 µm/min, competitive sample V=3.66 µm/min where V equals the rate of particle migration. Flocculation profiles and particle migration rates were not significantly different over the five-day period.

Example 2

Silicone Gum Emulsion Using Non-ionic Surfactant and an Amine-Functionalized Polyorganosiloxane as a co-emulsifier.

In a 150 mL polypropylene cup were added 65 grams of a silicone gum of a viscosity of 20 million cP, (as in Example 1) 10 grams of amino-functionalized organopolysiloxane with amine number >50 and viscosity <1000 cps (as Example 1). The contents were mixed in a Speed Mixer™ DAC 150FV for 60 seconds at 3400 rpm. The process was repeated until homogenous. To the contents was added 0.5 grams glacial acetic acid and a total of 5 grams of water over several additions assuring the mixture remained homogenous. To the mixture 2 grams of Tergitol 15-S-30 and a total of 5 grams water was added over several additions assuring the mixture remained homogenous. To the mixture 3 grams of Tergitol 15-S-30 and a total of 10 grams water was added over several additions assuring the mixture remain homogenous. The resulting mixture was a thick white to slightly yellow emulsion with particle size Mv=5.2 µm, $D_{90}$=8.1 µm, $D_{99}$=11.8 µm.

Example 3

Silicone Gum Emulsion Using a Silicone Polyether (SPE) and Non-Ionic Surfactant.

In a 150 mL polypropylene cup were added 65 grams of a silicone gum of a viscosity of 20 million cP (as in Example 1), 5 of a EO/PO block co-polymer silicone glycol (cloud point 98 C) (as in Example 1). The contents were mixed in the Speed Mixer™ DAC 150FV for 60 seconds at 3400 rpm. The process was repeated until homogenous. To the contents was added a total of 5 grams of water over several additions assuring the mixture remain homogenous. To the mixture 2 grams of Tergitol 15-S-30 and a total of 5 grams water was added over several additions assuring the mixture remain homogenous. To the mixture 3 grams of Tergitol 15-S-30 and a total of 10 grams water was added over several additions assuring the mixture remain homogenous. The resulting mixture failed to form an emulsion. Competitive sample Data: Particle size Mv=4.7 µm, $D_{90}$=6.6 µm, $D_{99}$=8.7 µm.

Example 4

Silicone Gum Emulsion Using Non-ionic Surfactant and an Amine-Functionalized Polyorganosiloxane as a co-emulsifier in a change-can mixer In a 2-gallon Charles Ross & Sons (NY) change-can mixer with glycol cooling system set to 0° C., 1950 grams of a silicone gum of a viscosity of 20 million cP (as in Example 1) and 240 grams of amino-functionalized organopolysiloxane with amine number >50 and viscosity <1000 cps (as in Example 1) (ICM Products Inc.) were mixed in a change-can mixed equipped with two high speed disperser blades and a scraper blade to adequately disperse the material. After mixing to homogenous, 50 grams of water, 90 grams of Tergitol 15-S-30 and 12 grams of acetic acid were added under high shear until homogenous. To the contents, 50 grams of water and 120 grams of Tergitol 15-S-7 (polyglycol ether; CAS Number 68131-40-8) were added under high shear until homogenous. To the contents 50 grams of water and 90 grams of Tergitol 15-S-30 were added under high shear until homogenous. A total of 345 grams water was added over several additions assuring the mixture remained homogenous. The resulting mixture was a thick white to slightly yellow emulsion with particle size Mv=2.38 µm, $D_{90}$=3.44 µm, $D_{99}$=4.92 µm.

Example 5

Silicone Gum Emulsion Using Laurel Alcohol Non-ionic Surfactants and an Amine-Functionalized Siloxane as a Co-Emulsifier.

In a 150 mL polypropylene cup were added 65 grams of a silicone gum, Xiameter RBG-9010 Gum, 6 grams of amino-functionalized siloxane with nitrogen content 0.4% and viscosity 3000 cps (Hansa ASR 7045 from CHT Germany GmbH), 4 grams laureth-4 (CAS: 9002-92-0) and 6 grams laureth-23 (CAS: 9002-92-0). The content was mixed in the Speed Mixer™ DAC 150FV for 60 seconds at 3400 rpm. The process was repeated until homogenous, assuring the product temperature does not exceed 45° C. To the content was added 0.35 grams glacial acetic acid and a total of 5 grams of water over several additions assuring the mixture remain homogenous. To the mixture a total of 14 grams water was added over several additions assuring the mixture remain homogenous. The resulting mixture was a thick white to slightly yellow emulsion with particle size Mv=3.2 µm, $D_{90}$=4.8 µm, $D_{99}$=6.5 µm.

Example 6

Silicone Gum Emulsion Using Laurel Alcohol Non-ionic Surfactants and No Amine-Functionalized Siloxane as a Co-Emulsifier.

In a 150 mL polypropylene cup were added 65 grams of a silicone gum, Xiameter RBG-9010 Gum, 4 grams laureth-4 (CAS: 9002-92-0) and 6 grams laureth-23 (CAS: 9002-92-0). The content was mixed in the Speed Mixer™ DAC 150FV for 60 seconds at 3400 rpm. The process was repeated until homogenous assuring the product temperature does not exceed 45° C. To the content was added 0.35 grams glacial acetic acid and a total of 5 grams of water over several additions assuring the mixture remain homogenous. To the mixture a total of 14 grams water was added over several additions assuring the mixture remain homogenous. The resulting mixture was a thick white to slightly yellow emulsion with particle size Mv=40.5 µm, $D_{90}$=75.2 µm, $D_{99}$=144.4 µm.

Example 7

Silicone Gum Emulsion Using Laurel Alcohol Non-ionic Surfactants and Amine-Functionalized Siloxane as a Co-Emulsifier.

In a 150 mL polypropylene cup were added 65 grams of a silicone gum, Xiameter RBG-9010 Gum, 6 grams of propoxytetramethyl piperidinyl dimethicone (CAS: 171543-65-0) (22502 BLUESIL FLD 21650 from Elkem Silicones USA Corp.) with viscosity of 96,000 cp and amine index of 18.48 meq, 4 grams laureth-4 (CAS: 9002-92-0) and 6 grams laureth-23 (CAS: 9002-92-0). The content was mixed in the Speed Mixer™ DAC 150FV for 60 seconds at 3400 rpm. The process was repeated until homogenous assuring the product temperature does not exceed 45° C. To the content was added 0.35 grams glacial acetic acid and a total of 5 grams of water over several additions assuring the mixture remain homogenous. To the mixture a total of 14 grams water was added over several additions assuring the mixture remain homogenous. The resulting mixture was a thick white to slightly yellow emulsion with particle size Mv=2.39 µm, $D_{90}$=3.63 µm, $D_{99}$=5.04 µm.

Example 8

Silicone Gum Emulsion Using Laurel Alcohol Non-ionic Surfactants and Amine-Functionalized Siloxane as a Co-Emulsifier.

In a 150 mL polypropylene cup were added 65 grams of a silicone gum, Xiameter RBG-9010 Gum, 12 grams of propoxytetramethyl piperidinyl dimethicone (CAS: 171543-65-0) (22502 BLUESIL FLD 21650 from Elkem Silicones USA Corp.) with viscosity of 96,000 cp and amine index of 18.48 meq, 4 grams laureth-4 (CAS: 9002-92-0) and 6 grams laureth-23 (CAS: 9002-92-0). The content was mixed in the Speed Mixer™ DAC 150FV for 60 seconds at 3400 rpm. The process was repeated until homogenous assuring the product temperature does not exceed 45° C. To the content was added 0.35 grams glacial acetic acid and a total of 5 grams of water over several additions assuring the mixture remain homogenous. To the mixture a total of 14 grams water was added over several additions assuring the mixture remain homogenous. The resulting mixture was a thick white to slightly yellow emulsion with particle size Mv=2.21 µm, $D_{90}$=2.94 µm, $D_{99}$=3.86 µm.

Example 9

Silicone Gum Emulsion Using Laurel Alcohol Non-ionic Surfactants and Amine-Functionalized Siloxane as a Co-Emulsifier with phosphoric acid.

In a 150 mL polypropylene cup were added 65 grams of a silicone gum, Xiameter RBG-9010 Gum, 6 grams of propoxytetramethyl piperidinyl dimethicone (CAS: 171543-65-0) (22502 BLUESIL FLD 21650 from Elkem Silicones USA Corp.) with viscosity of 96,000 cp and amine index of 18.48 meq, 4 grams laureth-4 (CAS: 9002-92-0) and 6 grams laureth-23 (CAS: 9002-92-0). The content was mixed in the Speed Mixer™ DAC 150FV for 60 seconds at 3400 rpm. The process was repeated until homogenous assuring the product temperature does not exceed 45° C. To the content was added 0.25 grams 85% phosphoric acid and a total of 5 grams of water over several additions assuring the mixture remain homogenous. To the mixture a total of 14 grams water was added over several additions assuring the mixture remain homogenous. The resulting mixture was a thick white to slightly yellow emulsion with particle size Mv=5.2 µm, $D_{90}$=7.16 µm, $D_{99}$=9.3 µm.

Example 10

Silicone Gum Emulsion Using Laurel Alcohol Non-ionic Surfactants and Amine-Functionalized Siloxane as a Co-Emulsifier with no acid.

In a 150 mL polypropylene cup were added 65 grams of a silicone gum, Xiameter RBG-9010 Gum, 6 grams of propoxytetramethyl piperidinyl dimethicone (CAS: 171543-65-0) (22502 BLUESIL FLD 21650 from Elkem Silicones USA Corp.) with viscosity of 96,000 cp and amine index of 18.48 meq, 4 grams laureth-4 (CAS: 9002-92-0) and 6 grams laureth-23 (CAS: 9002-92-0). The content was mixed in the Speed Mixer™ DAC 150FV for 60 seconds at 3400 rpm. The process was repeated until homogenous assuring the product temperature does not exceed 45° C. To the content was added a total of 5 grams of water over several additions assuring the mixture remain homogenous. To the mixture a total of 14 grams water was added over several additions assuring the mixture remain homogenous. The resulting mixture was a thick white to slightly yellow emulsion with particle size Mv=15.15 µm, $D_{90}$=25.67 µm, $D_{99}$=36.91 µm.

Example 11

Silicone Gum Emulsion Using Tergitol Non-ionic Surfactants and Reduced Amine-Functionalized Siloxane as a Co-Emulsifier.

In a 2-gallon Charles Ross & Sons (NY) change-can mixer with glycol cooling system set to 0° C., 2031 grams of a silicone gum, Xiameter RBG-9010 Gum, and 125 grams of amino-functionalized organopolysiloxane with nitrogen content 0.4% and viscosity 3000 cps (Hansa ASR 7045 from CHT Germany GmbH) were mixed in a change-can mixed equipped with two high speed disperser blades and a scraper blade to adequately disperse the material. After mixing to homogenous, 60 grams of water, 94 grams of Tergitol 15-S-30 and 12.5 grams of acetic acid were added under high shear until homogenous. To the contents, 60 grams of water and 94 grams of Tergitol 15-S-9 (polyglycol ether; CAS Number 68131-40-8) were added under high shear until homogenous. To the contents 60 grams of water and 94 grams of Tergitol 15-S-30 were added under high shear until homogenous. A total of 336 grams water was added over several additions assuring the mixture remained homogenous. The resulting mixture was a thick white to slightly yellow emulsion with particle size Mv=1.08 µm, $D_{90}$=1.40 µm, $D_{99}$=1.75 µm.

Example 12

Silicone Gum Emulsion Using Laurel Alcohol Non-ionic Surfactants and an Amine-Functionalized Siloxane as a Co-Emulsifier.

In a 150 mL polypropylene cup were added 65 grams of a silicone gum, BLUESIL™ Gum FB (Elkem Silicones France), 6 grams of amino-functionalized siloxane with nitrogen content 0.4% and viscosity 3000 cps (Hansa ASR 7045 from CHT Germany GmbH), 4 grams laureth-4 (CAS: 9002-92-0) and 6 grams laureth-23 (CAS: 9002-92-0). The content was mixed in the Speed Mixer™ DAC 150FV for 60 seconds at 3400 rpm. The process was repeated until homogenous, assuring the product temperature does not exceed 45° C. To the content was added 0.35 grams glacial acetic acid and a total of 5 grams of water over several additions assuring the mixture remain homogenous. To the mixture a total of 14 grams water was added over several additions assuring the mixture remain homogenous. The resulting mixture was a thick white to slightly yellow emulsion with particle size Mv=2.37 µm, $D_{90}$=3.31 µm, $D_{99}$=4.31 µm.

Example 13

Silicone Gum Emulsion Using Laurel Alcohol Non-ionic Surfactants and an Amine-Functionalized Siloxane as a Co-Emulsifier.

In a 150 mL polypropylene cup were added 65 grams of a silicone gum, Shin-Etsu KE-76BS Gum (Shin-Etsu Silicones of America), 6 grams of amino-functionalized siloxane with nitrogen content 0.4% and viscosity 3000 cps (Hansa ASR 7045 from CHT Germany GmbH), 4 grams laureth-4 (CAS: 9002-92-0) and 6 grams laureth-23 (CAS: 9002-92-0). The content was mixed in the Speed Mixer™ DAC 150FV for 60 seconds at 3400 rpm. The process was repeated until homogenous, assuring the product temperature does not exceed 45° C. To the content was added 0.35 grams glacial acetic acid and a total of 5 grams of water over several additions assuring the mixture remain homogenous. To the mixture a total of 14 grams water was added over several additions assuring the mixture remain homogenous. The resulting mixture was a thick white to slightly yellow emulsion with particle size Mv=3.54 µm, $D_{90}$=5.87 µm, $D_{99}$=9.56 µm.

TABLE 1

Shows the particle size data of emulsions produced via examples 11 & 7 versus two top commercially available products.
Competitor Product 1 is Dow Chemical Company DOWSIL™ 51 Additive and Competitor
Product 2 is Evonik TEGO ® Glide 482. Product 1 is a water dispersible ultrahigh molecular weight polydimethyl silicone dispersion with silanol functionality.
Product 2 is an emulsion of a high molecular weight polydimethylsiloxane.

| Product | $D_{50}$ Particle Size (µm) | $D_{90}$ Particle Size |
|---|---|---|
| Example 11 | 1.08 | 1.75 |
| Example 7 | 2.39 | 3.63 |
| Competitor Product 1 | 3.27 | 5.65 |
| Competitor Product 2 | 0.83 | 1.35 |

TABLE 2

Describes the stability or separation of each emulsion diluted to 30% non-volatile content then subjected to centrifugation at 3000 RPM for 30 minutes.

| Product | Stability |
|---|---|
| 5 | 5% creaming |
| 6 | Complete separation (60% settling, 40% creaming) |
| 7 | 5% cream |
| 8 | 5% cream, 10% settling |
| 9 | 15% settling, 20% cream |
| 10 | Complete separation (60% settling, 40% creaming) |
| 11 | Trace to no separation |

Centrifugation for 30 min is a stringent test the stresses the emulsion significantly. Trace to nothing is ideal as example 11 has (it also has the best particle size) the emulsion would be stable for extended period of time, >6 months without significant separation. 5% cream is acceptable as it is an indication the emulsion is stable but would eventually separate. 20% or greater cream would be an indication that the emulsion would probably separate within a shorter period of time weeks to 6 months.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A homogenous emulsion comprising:
   about 10 parts to about 80 parts of a silicone gum;
   about 1 part to about 20 parts of an amino-functionalized organopolysiloxane;
   about 1 part to about 20 parts of a nonionic surfactant;
   about 0.01 to about 5 parts acid;
   optionally, a silicone polyether; and
   optionally, an aqueous solution to equal 100 parts of total emulsion, wherein the particle size of the emulsion comprises an Mv that is from about 1 µm to about 5.5 µm; a $D_{90}$ is from about 1.3 µm to about 8.5 µm and a $D_{99}$ is from about 1.5 µm to about 12 µm.

2. The emulsion of claim 1, wherein the silicone gum comprises about 50 to about 70 parts.

3. The emulsion of claim 1, wherein the silicone gum comprises about 65 parts.

4. The emulsion of claim 1, wherein the silicone gum comprises a homopolymer of dimethylsiloxane or is a hydroxyl terminated dimethylsiloxane.

5. The emulsion of claim 1, wherein the silicone gum is a polydimethylsiloxane gum having a viscosity of at least 10 million cP at 25° C. at 0.01 Hz.

6. The emulsion of claim 1, wherein the silicone gum is a hydroxy terminated polydimethylsiloxane gum having a viscosity of at least 10 million cP at 25° C. at 0.01 Hz.

7. The emulsion of claim 1, wherein the amino-functionalized organopolysiloxane comprises about 5 parts to about 15 parts.

8. The emulsion of claim 7, wherein the amino-functionalized organopolysiloxane comprises about 10 parts.

9. The emulsion of claim 1, wherein the amino-functionalized organopolysiloxane comprises the formula:

$$[R_3SiO_{1/2}][R_2SiO_{2/2}]_a[RR^NSiO_{2/2}]_b[R_3SiO_{1/2}]$$

wherein; a is 1-1000;
b is 1-100;
each R is independently a monovalent organic group;
$R^N$ is $-R^3NHR^4$, $-R^3NR_2^4$, or $R^3NHR^3NHR^4$;
each $R^3$ is a $C_2$-$C_{20}$ alkyl group; and
each $R^4$ is a hydrogen or a $C_1$-$C_{20}$ alkyl group.

10. The emulsion of claim 1, wherein the amino-functionalized organopolysiloxane comprises a $R^4N^+X^-$ quaternary ammonium siloxane.

11. The emulsion of claim 1, wherein the nonionic surfactant comprises a secondary alcohol ethoxylate.

12. The emulsion of claim 1, wherein the optional silicone polyether is present from about 2 parts to about 15 parts.

13. The emulsion of claim 1, wherein the optional silicone polyether is an ethylene oxide/propylene oxide block copolymer silicone glycol.

14. The emulsion of claim 1, wherein the acid is a carboxyl acid, organic acid or an inorganic mineral acid.

15. The emulsion of claim 14, wherein the acid is acetic acid.

16. The emulsion of claim 1, wherein the composition is an emulsion.

17. The emulsion of claim 1, wherein the emulsion does not include an aromatic solvent.

18. The emulsion of claim 1, further comprising a non-aromatic solvent.

19. The emulsion of claim 18, wherein the non-aromatic solvent is a $C_1$-$C_{20}$ alkyl or alkylene monohydridic or polyhydridic alcohol.

* * * * *